(12) United States Patent
Nair et al.

(10) Patent No.: US 10,508,128 B2
(45) Date of Patent: Dec. 17, 2019

(54) PROCESS FOR THE PREPARATION OF SGLT INHIBITOR COMPOUNDS

(71) Applicant: INDOCO REMEDIES LIMITED, Mumbai (IN)

(72) Inventors: Ranjeet Nair, Navi Mumbai (IN); Palangat Vayalileveetil Ramesan, Navi Mumbai (IN); Sandip Kacharu Deshmukh, Navi Mumbai (IN); Aditi Milind Panandikar, Mumbai (IN)

(73) Assignee: Indoco Remedies Limited, Mumbai, Maharashtra (IN)

( * ) Notice: Subject to any disclaimer, the term of this patent is extended or adjusted under 35 U.S.C. 154(b) by 71 days.

(21) Appl. No.: 15/548,713

(22) PCT Filed: Feb. 9, 2016

(86) PCT No.: PCT/IN2016/050048
§ 371 (c)(1),
(2) Date: Aug. 3, 2017

(87) PCT Pub. No.: WO2016/128995
PCT Pub. Date: Aug. 18, 2016

(65) Prior Publication Data
US 2018/0016290 A1    Jan. 18, 2018

(30) Foreign Application Priority Data

Feb. 9, 2015 (IN) ............................ 417/MUM/2015
Apr. 27, 2015 (IN) .......................... 1683/MUM/2015

(51) Int. Cl.
*C07H 7/04* (2006.01)
*C07H 1/00* (2006.01)

(52) U.S. Cl.
CPC ...................................... *C07H 7/04* (2013.01)

(58) Field of Classification Search
None
See application file for complete search history.

(56) References Cited

FOREIGN PATENT DOCUMENTS

| CN | 105440025 A | 3/2016 | | |
|---|---|---|---|---|
| EP | 1 609 785 A1 | 12/2005 | | |
| WO | WO-0127128 A1 * | 4/2001 | ............ | A61K 31/70 |
| WO | WO 2005/092877 A1 | 10/2005 | | |
| WO | WO 2006/108842 A1 | 10/2006 | | |
| WO | WO 2006/120208 A1 | 11/2006 | | |
| WO | WO 2016/041470 A1 | 3/2016 | | |

OTHER PUBLICATIONS

Zheng, WO 2014/206299 A1, Dec. 31, 2014, machine translation. (Year: 2014).*
Mascitti, Med. Chem. Commun., 2013, 4, 101. (Year: 2013).*
CN103980261A, Aug. 13, 2014, machine translation. (Year: 2014).*
Komoroski, Clinical Pharmacology & Therapeutics, vol. 85, No. 5, May 2009.*
Deshpande et al., "A Practical Stereoselective Synthesis and Novel Cocrystallizations of an Amphiphatic SGLT-2 Inhibitor", Organic Process Research and Development, vol. 16, No. 4, Apr. 20, 2012.

* cited by examiner

*Primary Examiner* — Layla D Berry
(74) *Attorney, Agent, or Firm* — Kramer Amado P.C.

(57) ABSTRACT

The present invention DISCLOSES a novel process for preparing sodium glucose transporters 2 (SGLT2) inhibitor compounds of Formula IX.

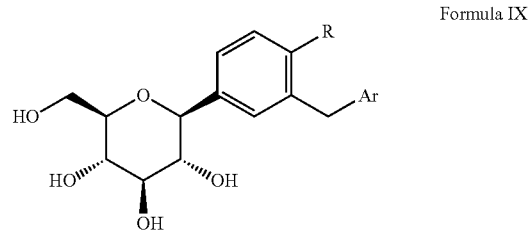

Formula IX

Wherein, R is halogen, alkyl or alkoxy group; and
Ar is aryl group, substituted or unsubstituted monocyclic polycyclic or heterocyclic ring selected from the residues A, B, C or D as given below,

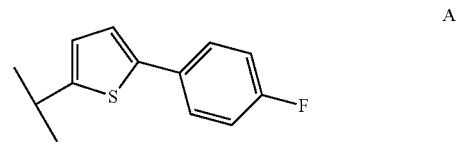

A

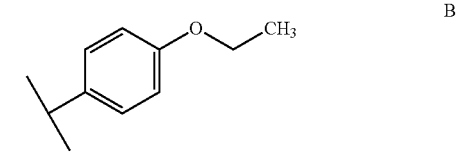

B

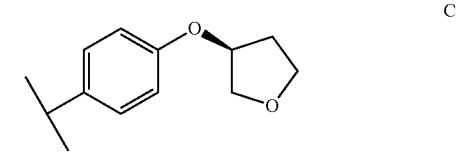

C

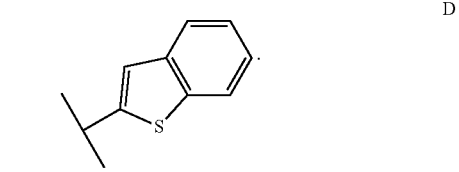

D

15 Claims, No Drawings

PROCESS FOR THE PREPARATION OF SGLT INHIBITOR COMPOUNDS

CROSS REFERENCE TO RELATED APPLICATIONS

This application claims the benefit of Indian Provisional application 417/MUM/2015 filed on Sep. 2, 2015 and 1683/MUM/2015 filed on 27 Apr. 2015 entitled "process for the preparation of SGLT inhibitor compounds" which is incorporated herein by reference.

FIELD OF THE INVENTION

The present invention relates to a novel process for preparing sodium glucose transporters 2 (SGLT2) inhibitor compounds of Formula IX.

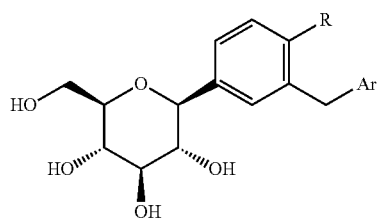

Formula IX wherein, R is halogen, alkyl or alkoxy group; and
Ar is aryl group, substituted or unsustituted monocyclic polycyclic or heterocyclic ring selected from the residues A, B, C or D as given below.

A
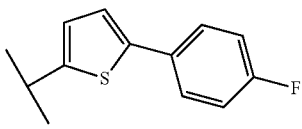

B
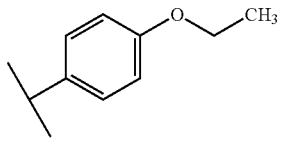

C
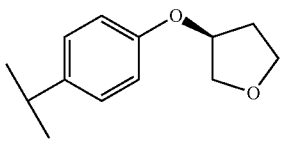

D
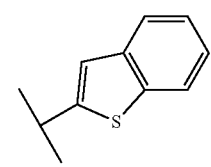

BACKGROUND AND PRIOR ART

Chronic hyperglycaemia is a defining feature of diabetes mellitus, and consequent glucotoxicity most likely accounts for the associated microvascular disease, and contributes to premature macrovascular disease. Hence early and effective glycaemic control is fundamental to therapeutic intervention. There are two types of diabetes more prevalent viz. type 1 diabetes and type 2 diabetes. In type 1 diabetes, hyperglycaemia is due to complete or almost complete loss of insulin-secreting β cells from the pancreatic islets of Langerhans. In type 2 diabetes, however, hyperglycaemia indicates insulin resistance coupled with abnormalities of insulin production and secretion and other endocrinopathies that collectively cause a highly heterogeneous and progressive disorder. Treatment of type 2 diabetes is often complicated by coexistent obesity, which further impairs insulin action and aggravates hypertension, dyslipidemia, inflammation, and other pathogenic factors that promote cardiovascular risk. New types of glucose-lowering drugs are needed, preferably offering complementary and additional effectiveness to existing drugs, along with benefits against any of the common accompanying disorders such as obesity and cardiovascular disease.

Sodium-glucose cotransporters inhibitors (SGLTs), such as SGLT1 and SGLT2 inhibitors provide new therapeutic targets to reduce hyperglycaemia in patients with diabetes. SGLT1 enables the small intestine to absorb glucose and contributes to the reabsorption of glucose filtered by the kidney. SGLT2 is responsible for reabsorption of most of the glucose filtered by the kidney. Inhibitors with varying specificities for these transporters can slow the rate of intestinal glucose absorption and increase the renal elimination of glucose into the urine.

Currently various SGLT2 inhibitor drugs have been approved or in clinical phase for treatment of type 2 diabetes. A significant numbers of SGLT2 are β-C-arylglucosides derived drug candidates, most of which comprises a central 1-deoxyglucose ring moiety that is arylated at C1. Among β-C-arylglucosides the pharmaceutically valuable drugs that are now being marketed are Canagliflogin (Formula II), Dapagliflogin (Formula III), Empagliflogin (Formula IV), whereas Ipragliflogin (Formula V) is approved for marketing in Japan. The structures of these compounds are as given below:

Formula II

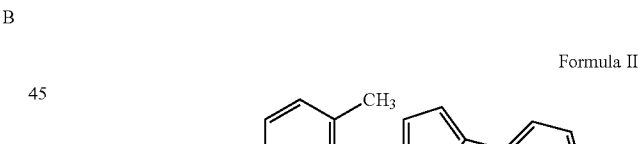

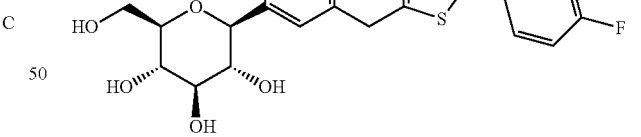

Formula III

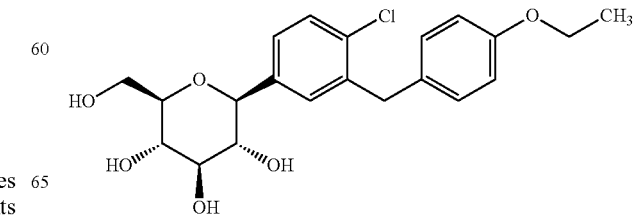

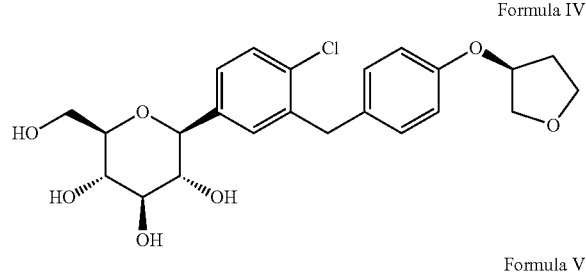

Formula IV

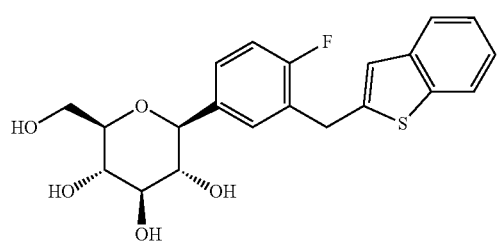

Formula V

There are various patents and patent applications viz., U.S. Pat. No. 6,515,117, U.S. Pat. No. 7,579,449, U.S. Pat. No. 7,772,407, U.S. Pat. No. 7,943,788, WO 2009035969, WO 2004063209, WO 2010022313, WO 2010043682, WO 2011047113, and WO 2013152476 which discloses the process for the preparation of these SGLT2 inhibitors. Most of these processes involve glucose or glucono lactone moiety for the preparation of the required compound.

In one of the prior art processes, hydroxyl group of the gluconolactone moiety is protected with trimethylsilane. The process discloses the reaction where after the C—C bond formation the resultant hemiketal formed is methylated using methanesulphonic acid. During the process the trimethylsilyl groups are hydrolysed and get removed. The demethylation of the methoxy group requires again protection with acetyl group followed by deacetylation to isolate the required compound that results in increased number of steps.

Another process discloses the protection of hydroxyl group of the gluconolactone moiety with acetyl group using controlled substance acetic anhydride. The protected gluconolactone is not available commercially and has to be prepared before the reaction.

Yet another process disclosed in the prior art, where the protection of hydroxyl group of the glucose moiety is carried out with pivaloyl chloride to get the compound pivaloyl-D-glucopyranose. Before the C—C bond formation, the pivaloyl-D-glucopyranose is reacted with bromine reagent to yield pivaloyl glucopyranosyl bromide compound which increases the number of steps and handling of bromine reagent.

The drawbacks of the above prior arts are:
1. The compounds glucose or gluconolactone when protected with pivaloyl, acetyl or trimethylsilyl groups need to be freshly prepared as the resultant compounds are unstable and not available on commercial scale.
2. The lack of stereoselectivity during formation of β-C-aryl glucoside reduces the yield of the product.
3. The process requires couple of protection and deprotection of the glucose moiety, which increases the number of steps and loss in yield of the final compound making the process uneconomical and cumbersome.
4. The glucose compound when protected with pivaloyl group requires the pivaloyl-D-glucopyranose compound to react with bromine reagent which increases the process cost and the number of steps and also involves the problem of handling of bromine reagent.

In view of the above, there remains a need for stereoselective, more efficient and economic process for the preparation of β-C-arylglucosides. The present inventors ameliorates the prior art drawbacks by using the commercially available and stable Benzyl-D-glucopyranose moiety for the C—C bond formation reaction in the presence of strong alkali.

OBJECTIVE OF THE INVENTION

The objective of the present invention is to develop a rigid and cost effective process for the preparation of sodium glucose transporters 2 (SGLT2) compound of Formula IX,

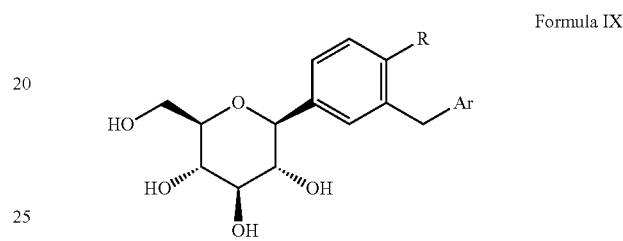

Formula IX wherein, R and Ar are as defined above

Another objective of the present invention is to develop a rigid and cost effective process for the preparation of an intermediate compound of Formula I, useful for the preparation of β-C-arylglucosides as sodium glucose transporters 2 (SGLT2) inhibitors,

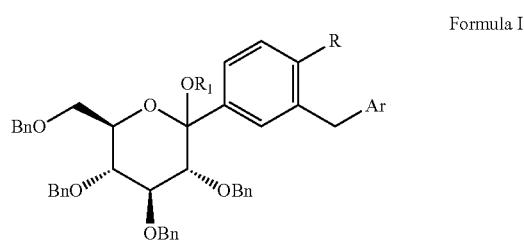

Formula I wherein, Bn is Benzyl group; $R_1$ is hydrogen or methyl; and R and Ar are as defined above.

Yet another objective of the present invention is to prepare β-C-arylglucosides with stereoselective orientation to prepare more of β anomer.

Yet another objective of the present invention is to carry out debenzylation using easily available cost effective reagent.

Yet another objective of the present invention is to prepare intermediate compound of Formula VIII

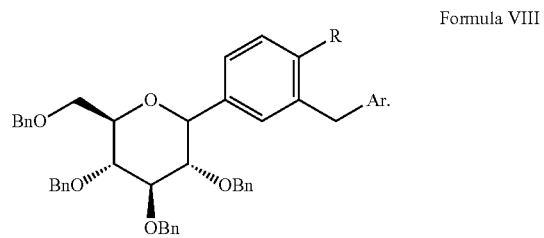

Formula VIII wherein, Bn, Ar and R are same as defined above.

Yet another objective of the present invention is to prepare intermediate compound of Formula VIIIa

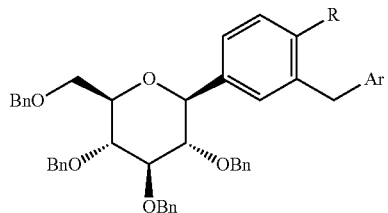

Formula VIIIa wherein, Bn, Ar and R are same as defined above.

SUMMARY OF THE INVENTION

Accordingly the present invention provides a process for the preparation of the of SGLT2 compound of Formula IX,

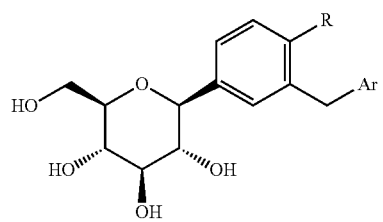

Formula IX wherein R is halogen, alkyl or alkoxy group; and
Ar is aryl group, substituted or unsustituted monocyclic, polycyclic or heterocyclic ring selected from the residues A, B, C or D as given below,

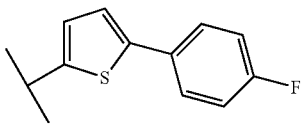

A

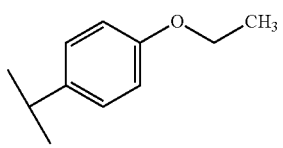

B

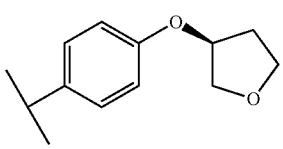

C

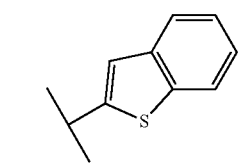

D which process comprises,
a) treating the compound 2,3,4,6-tetra-O-benzyl-D-glucopyranose of Formula VI,

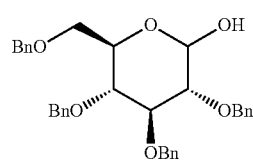

Formula VI with aryl halide compound of Formula VII

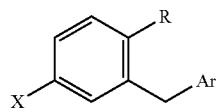

Formula VII wherein Ar and R is as previously defined and X is any halogen group selected from Cl, Br, or I in presence of sodium hypochlorite solution, a strong base and organic solvent at a temperature in the range of −80° C. to 0° C. to isolate an intermediate compound of Formula I,

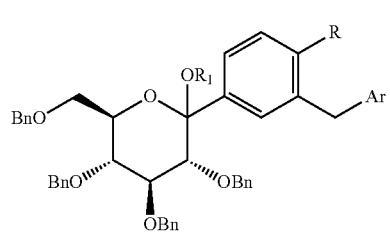

Formula I wherein Bn is Benzyl group;
$R_1$ is hydrogen or methyl; and R and Ar are as defined above.

b) reacting the intermediate compound of Formula I with a reducing reagent and boron trifluoride-diethyl etherate in presence of solvent to obtain the intermediate compound of Formula VIII.

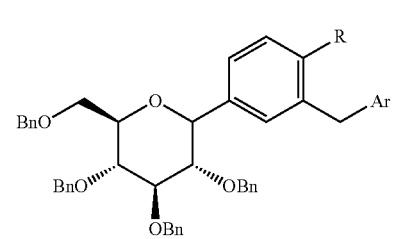

Formula VIII where R and Ar are as defined above c) purifying the compound of formula VIII from a solvent to obtain compound of formula VIIIa; and

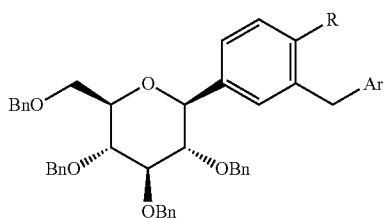

Formula VIIIa wherein, R, Ar and Bn are same as previously defined,
d) deprotecting the intermediate compound of Formula VIII to isolate compound of Formula IX.

In another aspect, the present invention provides the compound of Formula VIII

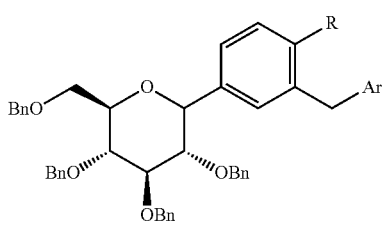

Formula VIII wherein, R and Ar are as defined above

In a further aspect, the present invention provides the process for the preparation of the compound canagliflozin of Formula II.

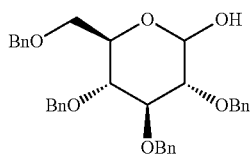

Formula II

Accordingly, the process comprising the steps of,
a) reacting the compound 2,3,4,6-tetra-O-benzyl-D-glucopyranose of Formula VI,

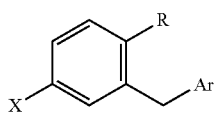

Formula VI with aryl halide compound of Formula VII

Formula VII wherein, X is any halogen group selected from Cl, Br or I; R is methyl; and Ar is 5-(4-fluorophenyl)thiophen-2-yl of Formula of residue A;

in presence of sodium hypochlorite solution, a strong base and organic solvent at a temperature in the range of −80° C. to 0° C. to isolate an intermediate compound (3R,4S,5R,6R)-3,4,5-tris(benzyloxy)-6-((benzyloxy)methyl)-2-(3-((5-(4-fluorophenyl)thiophen-2-yl)methyl)-4-methylphenyl)tetrahydro-2H-pyran-2-ol of Formula Ia,

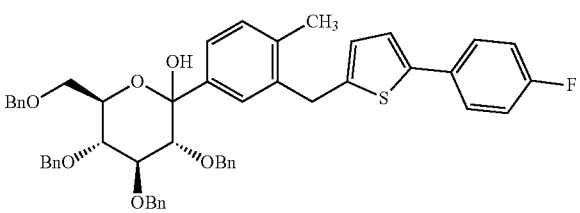

Formula Ia b) reacting the intermediate compound of Formula Ia with a reducing reagent and boron trifluoride-diethyl etherate in presence of solvent and further purifying to obtain the intermediate compound (2R,3R,4R,5S,6S)-3,4,5-tris(benzyloxy)-2-((benzyloxy)methyl)-6-(3-((5-(4-fluorophenyl)thiophen-2-yl)methyl)-4-methylphenyl)tetrahydro-2H-pyran of Formula VIIIb.

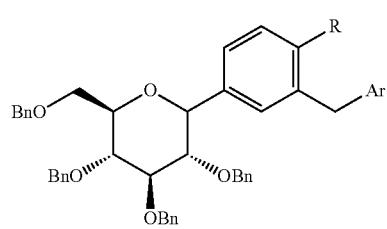

Formula VIII b c) deprotecting the compound of Formula VIII b to isolate compound of Formula II.

In another aspect, the present invention provides a compound of formula VIII

Formula VIII wherein, R is halogen, alkyl or alkoxy group; and Ar is aryl group, substituted or unsustituted monocyclic, polycyclic or heterocyclic ring selected from the residues A or B as given below.

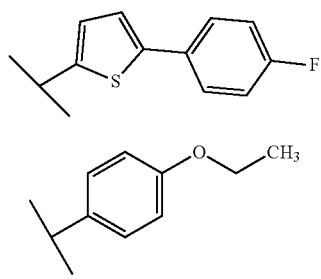

In yet another aspect, the present invention provides the compound of Formula VIIIa.

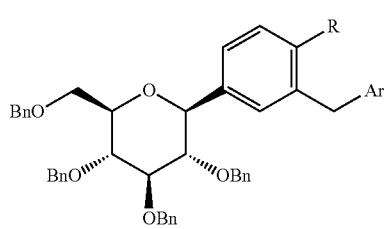

Formula VIIIa

In yet another aspect, the present invention provides the compound of Formula VIIIb.

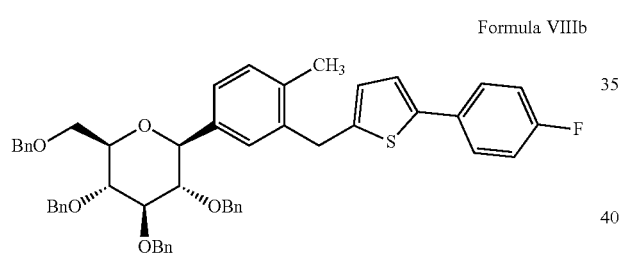

Formula VIIIb

In a further aspect, the present invention provides the compound of Formula VIIIc.

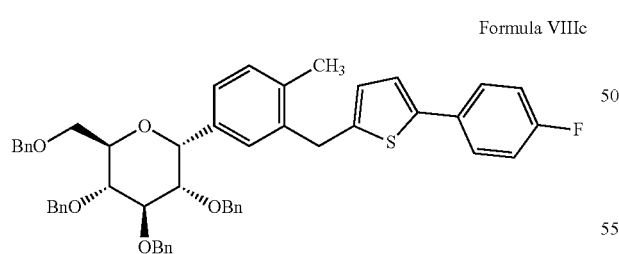

Formula VIIIc

DETAIL DESCRIPTION OF THE INVENTION

Unless specified otherwise, all technical and scientific terms used herein have the same meaning as commonly understood by one of ordinary skill in the art, to which this invention belongs. To describe the invention, certain terms are defined herein specifically as follows:

The present invention discloses a novel process for preparation of sodium glucose transporters 2 (SGLT2) inhibitor compounds of Formula IX, preferably the pharmaceutically useful antidiabetic compounds such as Canagliflozin, Dapagliflozin, Empagliflozin and Ipragliflozin.

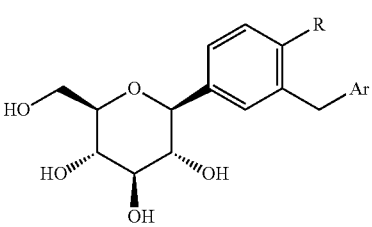

Formula IX wherein, R is halogen, alkyl or alkoxy group; and

Ar is aryl group, substituted or unsustituted monocyclic, polycyclic or heterocyclic ring selected from the residues A, B, C or D as given below,

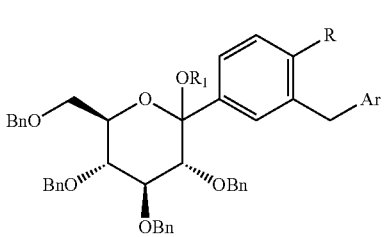

In one embodiment, the present invention provides a process for the synthesis of the compound of Formula I Formula I wherein, Bn is Benzyl group; $R_1$ is hydrogen or methyl;
R and Ar are same as defined above.

Accordingly, the process comprises treating the compound 2,3,4,6-tetra-O-benzyl-D-glucopyranose of Formula VI with aryl halide compound of Formula VII wherein Ar and R is as previously defined and X is any halogen group selected from Cl, Br, or I in presence of sodium hypochlorite solution, a strong base and organic solvent at a temperature in the range of −80° C. to 0° C.

The advantage of using 2,3,4,6-tetra-O-benzyl-D-glucopyranose over the other glucanone or glucose moiety is the stability of the compound at ambient temperature which makes the compound commercially available. The compound, 2,3,4,6-tetra-O-benzyl-D-glucopyranose due to its bulky structure produces more of the required β isomer and the hydroxyl protective group is more stable during the reaction and hence protection and deprotection steps are not required to isolate the pure compound.

Another embodiment of the present invention provides in situ preparation of 2,3,4,6-tetra-O-benzyl-D-gluconolactone. The compound of Formula VI was first reacted with sodium hypochlorite solution in presence of buffer and catalyst using water as solvent medium to prepare solution of 2,3,4,6-tetra-O-benzyl-D-gluconolactone by maintaining the temperature of the reaction at −5° C. to 30° C. and pH of the reaction at 7.0 to 8.0. The preferred buffer used for the reaction is sodium bicarbonate and acetic acid. The catalyst used for the reaction is 2,2,6,6-teteamethylpiperidine-1-oxyl either alone or in combination with potassium bromide.

The compound 2,3,4,6-tetra-O-benzyl-D-glucopyranose was charged in solvent and the catalyst is added to the solution. To this solution sodium hypochlorite solution in water was added by maintaining the temperature in the range of 10° C. to 40° C. The solvent used in the reaction is selected from group consisting of dichloromethane, dichloroethane, chloroform, toluene, xylene, tetrahydrofuran, ether, water either alone or in combinations thereof. The reaction completion was monitored on HPLC. The reaction mass was quenched by adding aqueous sodium thiosulphate solution. The reaction was worked up by separating the organic layer and concentrated to obtain solution of 2,3,4,6-tetra-O-benzyl-D-gluconolactone.

To the above solution under nitrogen the solution of aryl halide compound of Formula VII was charged and cooled the mixture to −70° C. The solvent used for preparing solution of the compound of Formula VII was selected from the group consisting of ether, diethyl ether, dibutyl ether, toluene, xylene and tetrahydrofuran either alone or in combinations thereof. The preferred solvent used is tetrahydrofuran. The reaction is carried out in presence of a base selected from organometallic reagents such as n-butyl lithium, sec-butyl lithium and mixture of n-hexyl lithium and (trimethylsilyl)methyl lithium. The preferred base used was n-butyl lithium. The reaction was monitored on HPLC for the completion. The reaction was worked up by quenching with aqueous sodium bicarbonate solution and brought the temperature of the reaction mixture slowly to 20° C. to 30° C. Separated the organic layer and extracted the aqueous layer with ethyl acetate. Combined the organic layer and washed the layer with brine solution. Concentrated the organic layer under reduced pressure to get residual mass of the hemiketal compound of Formula I. The residual mass was further treated with solvent mixture of ethyl acetate and methanol to isolate hemiketal compound of Formula I.

In another embodiment of the present invention, the compound of Formula I was subjected to reduction. The hemiketal compound was reduced with the reducing reagent and boron trifluoride-diethyl etherate in presence of solvent to obtain the compound of Formula VIII.

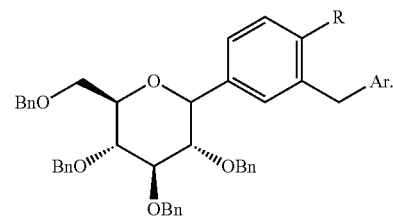

Formula VIII wherein R, Ar and Bn are same as previously defined.

The reducing reagents used for reduction of hemiketal was selected from the group of reagents, phenylsilane, tri-n-propylsilane, dimethylphenylsilane, triethylsilane, tris (trimethylsilyl)silane, triisobutylsilane, triphenylsilane, tert-butyldimethylsilane, triisopropylsilane and diisobutylaluminium hydride. The preferred reagent used are triethylsilane, phenylsilane, and tris(trimethylsilyl)silane whereas the most preferred reagents for the reduction used is triethylsilane. The solvent used for the reduction reaction was selected from the group of solvents such as dichloromethane, dichloroethane, chloroform, toluene, xylene, tetrahydrofuran, ether, ethyl acetate and acetonitrile either alone or in combinations thereof. The reaction was carried out at temperature in the range of −45° C. to 30° C. The preferred reaction temperature to carry out the reaction was −10° C. to 30° C., wherein the most preferred temperature of the reaction is 10° C. to 30° C. The completion of reaction was monitored on TLC/HPLC. After completion the reaction was quenched with water and neutralised the quenched mass with ammonia solution. Separated the organic layer and the aqueous layer was again extracted with ethyl acetate. The combined organic layers were washed with 10% brine solution and concentrated the solvent under vacuum at 40° C. to 45° C. to half. Charged methanol to the concentrated reaction mixture and heated to 64-65° C. The product was precipitated at 60° C. to 65° C. by adding additional portion of methanol and cooled to 25° C. to 30° C. Filtered the precipitated crude product to get the SGPLT2 compound of Formula VIII.

The crude compound of Formula VIII thus obtained after work up was purified from the solvent selected from the group of the solvents such as methanol, ethanol, Isopropyl alcohol, butanol and ethyl acetate either alone or in combinations thereof to obtain the desired pure β isomer of Formula VIIIa. The isolated pure compound of Formula VIIIa was taken for the preparation of SGPLT 2 inhibitors compounds.

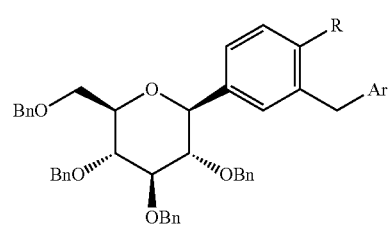

Formula VIIIa wherein R, Ar and Bn are same as previously defined.

The hemiketal compound of Formula I can also be taken for the reduction, by first methylating the hydroxy group compound at Cl and then carrying out reduction as per the above process.

Yet another embodiment of the present invention in which the reduced compound of Formula VIII or Formula VIIIa is deprotected/debenzylated using sodium iodide/boron trifluoride-diethyl etherate or Palladium/carbon or iodotrimethylsilane reagent in presence of solvent selected from the group consisting of acetonitrile, methanol, ethanol, isopropanol, tetrahydrofuran, diethyl ether, toluene, dichloromethane, dichloroethane, chloroform and water, either alone or in combinations thereof to yield the compound of Formula IX. The preferred deprotecting reagent used is sodium iodide/boron trifluoride-diethyl etherate. The temperature of the reaction is maintained in the range of 0° C. to 40° C. for 3-5 hours. The reaction was monitored on HPLC for the completion. After completion of the reaction the reaction mixture was quenched with triethyl amine at 25° C. to 30° C. and stirred for four hours, the precipitated solid mass was filtered. Charged the wet solid mass in water and made the pH acidic by using concentrated hydrochloric acid. The product was extracted using the solvent selected from the group consisting of methyl iso butyl ketone, methyl ethyl ketone and isopropyl acetate, wherein the preferred solvent used was methyl isobutyl ketone. The organic layer was washed with water. The solvent was concentrated under reduced pressure till half of the volume. The concentrated mass was precipitated by adding cyclohexane to isolate crude solid product of the compound of Formula IX.

In another embodiment of the present invention the crude compound of formula IX was purified using the solvents selected from the group consisting of ethyl acetate, methanol, methyl ethyl ketone, methyl isobutyl ketone, and isopropyl acetate either alone or in combinations thereof with water for dissolution of the crude compound and precipitating the pure compound adding the solvent selected from n-hexane, n-heptane, cyclohexane. The temperature range for the purification of the crude compound is maintained between 25° C. to 45° C.

The precipitated pure solid mass filtered to isolate the required pure SGPLT2 compound of Formula IX.

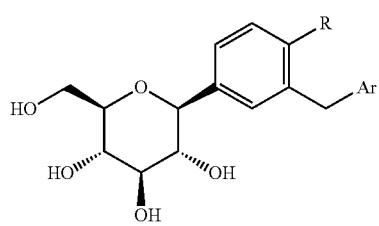

Formula IX wherein R is halogen, alkyl or alkoxy group and Ar is aryl group selected from the residues A, B, C or D as given below,

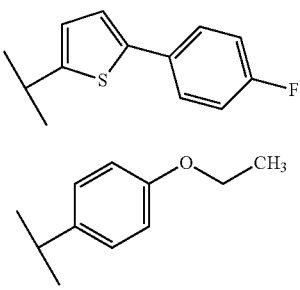

A

B

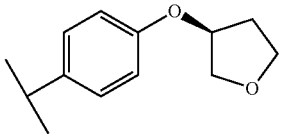

C

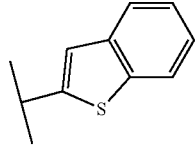

D

Another embodiment of the present invention provides the compound of Formula VIII b.

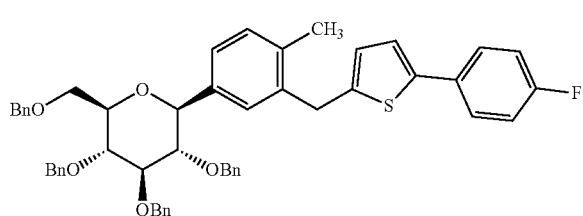

Formula VIII b

In yet another embodiment, the present invention provides the compound of Formula VIII c

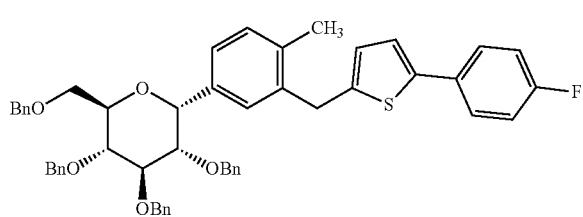

Formula VIII c

The present invention is further illustrated in detail with reference to the following examples. It is desired that the examples be considered in all respects as illustrative only and non restrictive to the invention.

EXAMPLES

Example 1

Stage 1: Synthesis of (3R,4S,5R,6R)-3,4,5-tris(benzyloxy)-6-((benzyloxy)methyl)-2-(34(5-(4-fluorophenyl)thiophen-2-yl)methyl)-4-methylphenyl)tetrahydro-2H-pyran-2-ol Charged water (175 ml) and sodium bicarbonate (14 gm) in RB flask (RBF) and stirred. It was cooled to 0 to 5° C. and 10% sodium hypochlorite solution (34.5 gm) was added. By maintaining the temperature between (0 to 5° C.), pH was adjusted with acetic acid to 7.0-7.5 (solution 1).

In another 500 ml 4 neck RBF, 2,3,4,6-tetra-O-benzyl-D-glucopyranose (25 gm, 0.0046 mol) dissolved in a 1:1 mixture of dichloromethane: toluene (150 ml) and charged water (50 ml). The compound 2,2,6,6-tetramethylpiperidine- 1-oxyl (0.1 gm) was then added to this mixture. To the above solution, sodium hypochlorite solution (solution 1) was slowly added by maintaining the temperature between 10° C. to 15° C. The progress of the reaction was monitored by HPLC. After completion of the reaction, the reaction mixture was quenched by adding aqueous sodium thiosulphate (11.25 gm in 25 ml water) solution. The quenched reaction mixture was stirred for 10-15 minutes and the temperature of reaction mixture was raised to 25° C. The organic layer was separated. The aqueous layer was extracted with toluene (2×75 ml) and separated. The combined organic layer was washed with water (3×150 ml). The organic layer (275 ml) was then dried over anhydrous sodium sulphate and concentrated under reduced pressure till to attain one third of its volume.

The above toluene layer was taken in 500 ml 4-necked RBF and a solution of (5-iodo-2-methyl-benzyl)-2-(4-fluorophenyl)thiophene (12.5 gm, 0.0306 moles) in tetrahydrofuran (75 ml) was added, under nitrogen atmosphere. Applied cooling to the resulting mixture to about −40° C. to −30° C., and charged n-butyl lithium in hexane 1.6M (37.5 ml, 0.0588 moles).

The reaction progress was monitored by HPLC. After the reaction completion, reaction was quenched with saturated sodium bicarbonate solution (25 ml) and was allowed to attain 25° C. to 30° C. The layers were separated and the organic layer, dried over sodium sulphate was concentrated under reduced pressure to yield the compound (3R,4S,5R, 6R)-3,4,5-tris(benzyloxy)-6-((benzyloxy)methyl)-2-(3-((5-(4-fluorophenyl)thiophen-2-yl)methyl)-4-methyl-phenyl) tetrahydro-2H-pyran-2-ol as a solid (25 gm, 65%).

Stage 2: Synthesis of (2R,3R,4R,5S,6S)-3,4,5-tris (benzyloxy)-2-((benzyloxy)methyl)-6-(3-((5-(4-fluorophenyl)thiophen-2-yl)methyl)-4-methylphenyl) tetrahydro-2H-pyran In 250 ml 4-neck RBF charged (3R,4S,5R,6R)-3,4,5-tris (benzyloxy)-6-((benzyloxy)methyl)-2-(3-((5-(4-fluorophenyl)thiophen-2-yl)methyl)-4-methylphenyl)tetrahydro-2H-pyran-2-ol (15 gm, 0.01829 mole) and dichloromethane (60 ml) under nitrogen atmosphere. The reaction mass cooled to −30° C. under stirring. Maintaining the temperature between −40° C. to −20° C. charged triethylsilane (8.6 ml, 0.0543 mol), followed by a slow addition of boron trifluoridediethyl etherate (7.2 ml, 0.0573 moles). After the addition was complete, maintained the reaction mass for 30 minutes and then removed the ice bath and allowed the temperature to attain 20° C. and maintained under nitrogen, for 1.0-2.0 hour. The reaction progress was monitored on TLC. After completion, the reaction mass was quenched with cold water (60 ml) and charged ethyl acetate (60 ml). The layers were separated and the organic layer was washed with a saturated sodium bicarbonate solution, dried over sodium sulfate and concentrated to yield the compound (2R,3R,4R,5S,6S)-3,4, 5-tris(benzyloxy)-2-((benzyloxy) methyl)-6-(3-((5-(4-fluorophenyl)-thiophen-2-yl)methyl)-4-methylphenyl) tetrahydro-2H-pyran (14.0 gm, 95%).

Stage 3: Synthesis of (2S,3R,4R,5S,6R)-2-(3-((5-(4-fluorophenyl)thiophen-2-yl)methyl)-4-methylphenyl)-6-(hydroxymethyl)tetrahydro-2H-pyran-3,4,5-triol [Canagliflozin]

In 250 ml RBF charged (3R,4R,5R,6R)-3,4,5-tris(benzyloxy)-6-(benzyloxymethyl)-2-(3-[(5-(4-fluorophenyl)thiophen-2-yl)-4-methylphenyl]tetrahydro-2H-pyran (10 gm, 0.0124 moles) and dichloromethane (100 ml). The reaction mixture was cooled under stirring to 0° C., and charged iodotrimethylsilane (8.83 ml, 0.062 moles). Raised the temp to 25° C.-30° C. and maintained for 5-6 hours. The reaction was monitored on TLC. The reaction mixture was concentrated under reduced pressure, charged cyclohexane to the residual mass and stirred. Filtered the precipitated compound and dried to isolate (2S,3R,4R,5S,6R)-2-(3-((5-(4-fluorophenyl)thiophen-2-yl)methyl)-4-methylphenyl)-6-(hydroxymethyl)tetrahydro-2H-pyran-3,4,5-triol as a solid (5.0 gm, 90%).

Example 2

Preparation of (2S,3R,4R,5S,6R)-2-(3-[(5-(4-flourophenyl)thiophene-2-yl)methyl]-4-methylphenyl)-6-(hydroxymethyl)tetrahydro-2H-pyran-3,4,5-triol [Canagliflozin]

In 4 neck RBF charged (3R,4R,5R,6R)-3,4,5-tris(benzyloxy)-6-(benzyloxymethyl)-2-(3-[(5-(4-fluorophenyl)thiophen-2-yl)-4-methylphenyl]tetrahydro-2H-pyran (50 gm, 0.0621 moles), dichloromethane (400 ml) and acetonitrile (300 ml), sodium iodide (100 gm, 0.667 moles), boron trifluoride-diethyl etherate (94.41 gm, 0.667 mole) at 25-30° C. along with acetonitrile (100 ml). The reaction mixture was stirred at room temperature for 4-5 hours. After reaction completion, the reaction mixture was quenched by 5% bicarbonate solution (400 ml) at 25-30° C. Separated the organic layer and aqueous layer was further extracted with dichloromethane (2×250 ml). Combined organic layer was washed with 5% thiosulfate solution and dried over anhydrous sodium sulphate. Filtered and the solvent was concentrated under reduced pressure. The residue was precipitated in cyclohexane (250 ml) to isolate crude (2S,3R,4R, 5S,6R)-2-(3-[(5-(4-flourophenyl)thiophene-2-yl)methyl]-4-methylphenyl)-6-(hydroxymethyl)tetrahydro-2H-pyran-3,4, 5-triol. The crude compound was further purified by dissolving in mixture of solvents ethyl acetate (100 ml) and water (2.0 ml). To the solution slowly charged n-hexane (100 ml) in reaction and stirred at 25° C.-30° C. for 12 hours and filtered the solid to isolate pure (2S,3R,4R,5S,6R)-2-(3-[(5-(4-flourophenyl)thiophene-2-yl)methyl]-4-methylphenyl)-6-(hydroxymethyl)tetrahydro-2H-pyran-3,4,5-triol (Canagliflozin) (22 gm, 80%).

Example 3

In situ preparation of (2S,3R,4R,5S,6R)-2-(3-[(5-(4-flourophenyl)thiophene-2-yl)methyl]-4-methylphenyl)-6-(hydroxymethyl)tetrahydro-2H-pyran-3,4,5-triol [Canagliflozin]

In a 250 ml 4-neck RBF under nitrogen atmosphere charged (3R,4S,5R,6R)-3,4,5-tris(benzyloxy)-6-(benzyloxymethyl)-2-(3-((5-(4-fluorophenyl)thiophen-2-yl) methyl)-4-methylphenyl)tetrahydro-2H-pyran-2-ol (50 gm, 0.0609 mole) and dichloromethane (200 ml). The reaction mass was cooled to −30° C. and charged triethylsilane (28.66 ml, 0.181 mole) followed by a slow addition of boron trifluoride-diethyl etherate (24.00 ml, 0.191 moles) maintaining the temperature at −40° C. to 0° C. After the addition was complete the ice bath was removed and the resulting mixture was stirred at room temperature, for 1.0-2.0 hrs monitoring the reaction progress by TLC.

After reaction completion, sodium iodide (100 gm, 0.667 moles) and boron trifluoride-diethyl etherate (94.41 gm, 0.667 mole) were added to the reaction mass at 25° C.-30° C. along with acetonitrile (200 ml). The reaction mixture was stirred at room temperature for 4-5 hours and reaction progress was monitored by TLC. After reaction completion it was quenched by 5% sodium bicarbonate solution (400 ml) at 25° C.-30° C. Separated the organic layer and aqueous layer was extracted with additional dichloromethane (2×250 ml). The combined organic layer was washed with 5% sodium thiosulfate solution and dried over anhydrous sodium sulphate. The solvent was concentrated under reduced pressure. The residue was precipitated in cyclohexane (250 ml) to isolate the crude (2S,3R,4R,5S,6R)-2-(3-[(5-(4-flourophenyethiophene-2-yl)methyl]-4-methylphenyl)-6-(hydroxymethyl)tetrahydro-2H-pyran-3,4,5-triol. The crude compound was further purified by dissolving in mixture of solvents ethyl acetate (100 ml) and water (2.0 ml). To the solution slowly charged n-hexane (100 ml) in reaction and stirred at 25° C.-30° C. for 12 hours and filtered the solid to isolate pure (2S,3R,4R,5S,6R)-2-(3-[(5-(4-flourophenyl)thiophene-2-yl)methyl]-4-methylphenyl)-6-(hydroxymethyl)tetrahydro-2H-pyran-3,4,5-triol (Canagliflozin) (22 gm, 80%).

Example 4

Stage 1: Synthesis of (3R,4R,5R,6R)-3,4,5-tris(benzyloxy)-6-((benzyloxy) methyl)-2-(3-((5-(4-fluorophenyl)thiophen-2-yl)methyl)-4-methyl-phenyl) tetrahydro-2H-pyran-2-ol In 3.0 lit round bottom flask charged water (400 ml) and sodium bicarbonate (53.44 gm) at room temperature stirred for 30 minutes and charged acetic acid (26.63 gm) and potassium bromide (1.6 gm) under stirring for 15 minutes. The solution of 2, 3, 4, 6-tetra-O-benzyl-D-glucopyranose (200 gm, 0.37 mole) in dichloromethane (1000 ml) was added to the reaction solution. Reaction mass was cooled to 20° C. to 25° C. The compound 2, 2, 6, 6,-tetramethylpiperidine-1-oxyl (0.8 gm.) was added to the reaction mass and charged slowly 10% sodium hypochlorite (325 gm (0.436) solution maintaining the temperature between 20° C. to 35° C. The progress of the reaction was monitored by HPLC after completion of the reaction, the reaction mixture was quenched by adding aqueous sodium thiosulphate (50 gm in 200 ml water) solution. Reaction mixture was stirred for 30 minutes. Separated the organic layer and extracted the aqueous layer with Dichloromethane (400 ml). The combined organic layer was washed twice with 10% brine solution. Distilled out the solvent under reduced pressure by maintaining the temperature below 45° C. to get the residual mass.

To the residual mass under nitrogen, charged solution of (5-Iodo-2-methyl-benzyl)-2-(4-fluoro-phenyl)thiophene (131 gm, 0.320 mole) dissolved in tetrahydrofuran (786 ml) and stirred. Applied cooling to the resulting mixture and brought the temperature to −70° C. Charged n-butyl lithium in hexane 1.6M (262 ml, 0.417 moles) maintaining the temperature between −70° C. to −30° C.

The reaction progress was monitored by HPLC. After the reaction completion, reaction was quenched with (10%) sodium bicarbonate solution (393 ml) and allowed the temperature to rise slowly to 25° C. to 30° C. Separated the organic layer and the aqueous layer was extracted with ethyl acetate (260 ml). The combined organic layer was washed with (10%) brine solution. Organic layer was concentrated under reduced pressure. The residue was dissolved in 1:1 mixture of solvent methanol and ethyl acetate at 50-55° C. The product was precipitated by adding methanol (4.0 Vol) at 50-55°. The reaction mass was cooled to 25-30° C. the solid was filtered to get (184 gm 70.2%) (3R, 4R, 5R, 6R)-3,4, 5-tris (benzyloxy)-6-((benzyloxy) methyl)-2-(3-((5-(4-fluorophenyl) thiophen-2-yl) methyl)-4-methyl-phenyl) tetrahydro-2H-pyran-2-ol.

Stage 2: Synthesis of (2R, 3R, 4R, 5S, 6S)-3, 4, 5-tris(benzyloxy)-2-((benzyloxy methyl)-6-(3-((5-(4-fluorophenyl)thiophen-2-yl)-4-methyl-phenyl] tetrahydro-2H-pyran In a 2.0 lit RBF charged (3R, 4R, 5R, 6R)-3, 4, 5-tris (benzyloxy)-6-((benzyloxy) methyl)-2-(3-((5-(4-fluorophenyl) thiophen-2-yl) methyl)-4-methyl-phenyl) tetrahydro-2H-pyran-2-ol (150 gm, 0.1829 mole) and ethyl acetate (900 ml) under nitrogen atmosphere. Maintaining the nitrogen atmosphere and stirring the reaction mass was cooled to 20° C. to 25° C. Triethyl silane (25.5 gm 0.21 mol) was added followed by a slow addition of boron trifluoride diethyl etherate (31.1 gm, 0.219 moles). After addition was complete, the reaction mixture was stirred maintaining the temperature at 25° C. to 30° C., for 1.0 to 2.0 hours. The reaction progress was monitored on TLC. After completion, the reaction mass was quenched with water (300 ml) and adjusted the pH between 7-10 using ammonia solution (25%). Separated the organic layer and aqueous layer was further extracted with ethyl acetate. The combined organic layers were washed with 10% brine solution, Organic layer was concentrated under vacuum below 45° C. to make the volume half. Charged methanol (3 vol) and heated the reaction mixture to 64° C. to 65° C. to get the clear solution. Precipitated the product by adding additional four volume methanol and cooled to 25° C. to 30° C. The solid product was filtered to get (105 gm 71.42%) (2R, 3R, 4R, 5S, 6S)-3, 4, 5-tris(benzyloxy)-2-((benzyloxymethyl)-6-(3-((5-(4-fluorophenyl)thiophen-2-yl)-4-methyl-phenyl]-tetrahydro-2H-pyran compound.

Stage 3: Preparation of (2S, 3R, 4R,5S,6R)-2-(3-[(5-(4-flourophenyl) thiophene-2-yl) methyl]-4methylphenyl)-6-(hydroxymethyl)tetrahydro-2H-pyran-3,4,5-triol [Canagliflozin]

In 2.0 lit RBF charged (2R,3R, 4R, 5S, 6S)-3, 4, 5-tris (benzyloxy)-2-((benzyloxy methyl)-6-(3-((5-(4-fluorophenyl)thiophen-2-yl)-4-methylphenyl]tetrahydro-2H-pyran (100 gm, 0.124 moles), acetonitrile (600 ml), sodium iodide (200 gm, 1.335 moles), water (25 ml), boron trifluoride diethyletherate (226 gm, 1.592 moles) maintaining temperature between 25° C. to 35° C. and flushed with acetonitrile (100 ml). The reaction mixture was stirred maintaining temperature at 25° C. to 35° C. for three hours. After reaction completion by TLC, the reaction mixture was quenched using triethyl amine (250 ml) and maintained under stirring at 25° C. to 30° C. for four hours. Filtered the solid mass and the wet cake was taken in water (500 ml). Adjusted the pH between 2-3 using concentrated hydrochloric acid. The product was extracted with Methyl Iso butyl ketone (500 ml), aqueous layer was once more extracted with Methyl Iso butyl ketone (200 ml). The combined organic layer was washed with water and concentrated under reduced pressure to bring the volume to half. To the concentrated volume charged cyclohexane (300 ml) to precipitate the crude product (40 gm) (2S, 3R, 4R, 5S, 6R)-2-(3-[(5-(4-flourophenyl) thiophene-2-yl) methyl]-

4methylphenyl)-6-(hydroxymethyl) tetrahydro-2H-pyran-3, 4, 5-triol (Crude Canagliflozin).

Purification of Crude Canagliflozin:

In 250 ml round bottom flask, crude Canagliflozin (40 gm) was dissolved in mixture of 2:1 ratio methyl isobutyl ketone and methanol at 25° C. to 30° C. After dissolving the solid charged activated charcoal (2.0 gm) and stirred for 30 minutes. Filtered the charcoal through hyflo bed. The filtrate was distilled under reduced pressure to obtain an oily residue. To this residue, charged methyl isobutyl ketone (160 ml), water (1.6 ml). The temperature of the reaction mass was raised to 30° C. to 35° C. and stirred for 30 minutes. Charged slowly cyclohexane (80 ml) maintaining the temperature at 30° C. to 35° C. After addition was completed reaction mass stirred for 3 hrs at same temperature then cooled to 25° C. to 30° C. The solid was filtered to obtain (35.2 gm), 88% of pure crystalline Canagliflozin.

Example 5

Preparation of (2S, 3R, 4R,5S,6R)-2-(3-[(5-(4-flourophenyl) thiophene-2-yl) methyl]-4methylphenyl)-6-(hydroxymethyl)tetrahydro-2H-pyran-3,4,5-triol [Canagliflozin]

In a 2.0 lit RBF charged (3R, 4R, 5R, 6R)-3, 4, 5-tris (benzyloxy)-6-((benzyloxy) methyl)-2-(3-((5-(4-fluorophenyl) thiophen-2-yl) methyl)-4-methyl-phenyl) tetrahydro-2H-pyran-2-ol (150 gm, 0.1829 mole) and ethyl acetate (900 ml) under nitrogen atmosphere. The reaction mass cooled to 20° C. to 25° C. under stirring. Triethyl silane (25.5 gm 0.21 mol) was added followed by a slow addition of boron trifluoride diethyl etherate (31.1 gm, 0.219 moles). After complete addition the reaction mixture was maintained under stirring at 25° C. to 30° C., for 1.0-2.0 hours. The reaction progress was monitored on TLC. After reaction completion Ethyl acetate was distilled out completely under reduced pressure.

To the residue charged acetonitrile (600 ml), sodium iodide (200 gm, 1.335 moles), purified water (25 ml), boron trifluoride diethyletherate (226 gm, 1.592 moles) at 25° C. to 30° C. and flushed with acetonitrile (100 ml). The reaction mixture was stirred at 30° C. to 35° C. for 3 hours. After reaction completion by TLC, the reaction mixture was quenched with triethyl amine (250 ml) and stirred for at 25° C. to 30° C. 4 hours. The solid mass was filtered and the wet cake taken in water (500 ml). Adjusted the pH between 2-3 using concentrated hydrochloric acid. The product was extracted with Methyl Iso butyl ketone (500 ml) and separated the layer. Extracted the aqueous layer with Methyl Iso butyl ketone (200 ml). Then combined organic layer was washed with purified water. The solvent was concentrated under reduced pressure to make the volume to half. Charged cyclohexane (300 ml) to the concentrated solution to precipitate (40 gm), crude (2S, 3R, 4R,5S,6R)-2-(3-[(5-(4-flourophenyl) thiophene-2-yl) methyl]-4methylphenyl)-6-(hydroxymethyl) tetrahydro-2H-pyran-3, 4, 5-triol (Canagliflozin).

Purification of Crude Canagliflozin:

In 250 ml round bottom flask, crude Canagliflozin (40 gm) was dissolved in mixture of 2:1 ratio methyl isobutyl ketone and methanol at 25° C. to 30° C. After dissolving the solid charged activated charcoal (2.0 gm) and stirred for 30 minutes. Filtered the charcoal through hyflo bed. The filtrate was distilled under reduced pressure to obtain an oily residue. To this residue, charged methyl isobutyl ketone (160 ml), water (1.6 ml). The temperature of the reaction mass was raised to 30° C. to 35° C. and stirred for 30 minutes. Charged slowly cyclohexane (80 ml) maintaining the temperature at 30° C. to 35° C. After addition was completed reaction mass stirred for 3 hrs at same temperature then cooled to 25° C. to 30° C. The solid was filtered to obtain (35.2 gm), 88% of pure crystalline Canagliflozin.

We claim:

1. A process for the preparation of a compound of Formula IX,

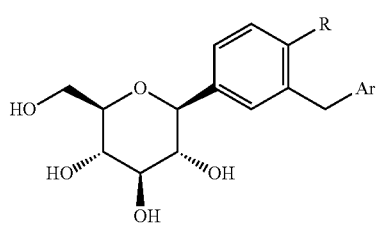

Formula IX wherein R is halogen, alkyl or alkoxy group; and Ar is aryl group, substituted or unsubstituted monocyclic, polycyclic or heterocyclic ring selected from the residues A, B, C or D as given below,

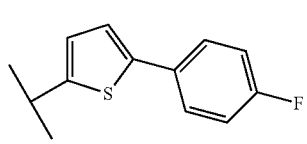

A

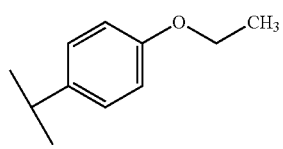

B

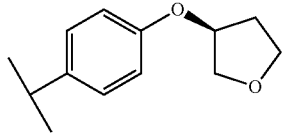

C

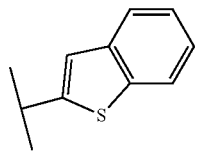

D said process comprising,
a) treating 2,3,4,6-tetra-O-benzyl-D-glucopyranose of Formula VI,

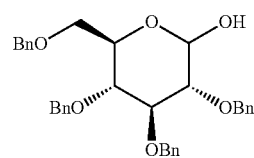

Formula VI with an aryl halide compound of Formula VII

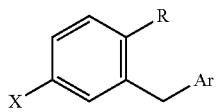

Formula VII wherein Ar and R are as previously defined and X is Cl, Br, or I;

in the presence of a sodium hypochlorite solution, a strong base, and an organic solvent at a temperature in the range of -80° C. to 0° C. to isolate an intermediate compound of Formula I;

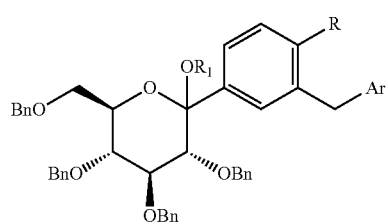

Formula I wherein Bn is Benzyl group; $R_1$ is hydrogen or methyl; and
R and Ar are as defined above;

b) reacting the intermediate compound of Formula I with triethyl silane and boron trifluoride-diethyl etherate in presence of a solvent to obtain an intermediate compound of Formula VIII, wherein the solvent is dichloromethane, dichloroethane, chloroform, ethyl acetate, or a mixture thereof;

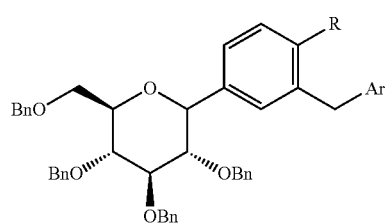

Formula VIII where R and Ar are as defined above, c) purifying the compound of formula VIII from a solvent to obtain an intermediate compound of formula VIIIa; and

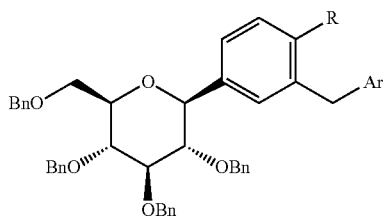

Formula VIIIa wherein R, Ar and Bn are same as previously defined; and d) deprotecting the intermediate compound of Formula VIIIa to isolate the compound of Formula IX.

2. The process according to claim 1, wherein, the organic solvent used in step a) is selected from the group consisting of ether, diethyl ether, dibutyl ether, toluene, xylene, tetrahydrofuran, and mixtures thereof.

3. The process according to claim 1, wherein, the base used in step a) is selected from the group consisting of organometallic reagents.

4. The process according to claim 1, wherein, the reaction of step b) is carried out at a temperature in the range of -45° C. to 30° C.

5. The process according to claim 1, wherein, the purification of the compound of Formula VIII is carried out in a solvent selected from the group consisting of methanol, ethanol, isopropyl alcohol, butanol, ethyl acetate and mixtures thereof to obtain compound of Formula VIIIa.

6. The process according to claim 1, wherein, the deprotection of formula VIIIa is conducted in presence of a reducing agent and a solvent at a temperature range of 0° C. to 40° C.

7. The process according to claim 6, wherein,
the reducing agent is sodium iodide/boron trifluoride-diethyl etherate, Palladium/carbon, iodotrimethylsilane reagent, or a mixture thereof; and
the solvent is selected from the group consisting of acetonitrile, methanol, ethanol, isopropanol, tetrahydrofuran, diethyl ether, toluene, dichloromethane, dichloroethane, chloroform, water, and mixtures thereof.

8. The process according to claim 1, wherein, the compound of formula IX is purified using a first solvent selected from the group consisting of ethyl acetate, methanol, methyl ethyl ketone, methyl isobutyl ketone, isopropyl acetate, and aqueous or nonaqueous mixtures thereof for dissolution; and using a second solvent selected from the group consisting of n-hexane, n-heptane, cyclohexane, and mixtures thereof for precipitation of the pure compound.

9. The process according to claim 8, wherein, the purification of the crude compound is maintained at a temperature of 25° C. to 45° C.

10. The process according to claim 1, wherein, the compound of formula IX is selected from the group of compounds consisting of
a) (2S,3R,4R,5S,6R)-2-(3-((5-(4-fluorophenyl)thiophen-2-yOmethyl)-4-methylphenyl)-6-(hydroxymethyl)tetrahydro-2H-pyran-3,4,5-triol of Formula II;

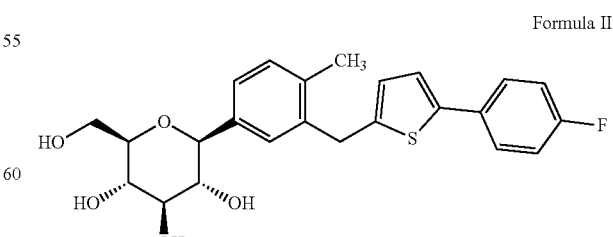

Formula II b) (2S,3R,4R,5S,6R)-2-[4-chloro-3-(4-ethoxybenzyl) phenyl]-6-(hydroxymethyl) tetrahydro-2H-pyran-3,4,5-triol of formula III;

Formula III

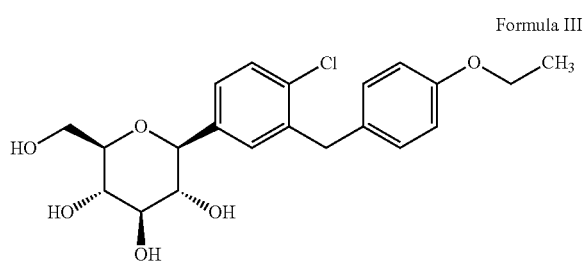 [SMILES: CCOc1ccc(Cc2cc([C@@H]3O[C@H](CO)[C@@H](O)[C@H](O)[C@H]3O)ccc2Cl)cc1]

c) (2S,3R,4R,5S,6R)-2-[4-chloro-3-[[4-[(3S)-oxolan-3-yl]oxyphenyl]methyl]phenyl]-6-(hydroxymethyl)oxane-3,4,5-triol of formula IV; and Formula IV

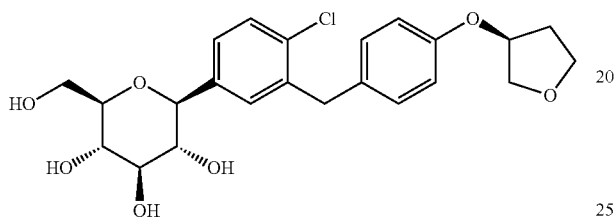

d) (2S,3R,4R,5S,6R)-2-[3-(1-benzothiophen-2-ylmethyl)-4-fluorophenyl]-6-(hydroxymethyl)oxane-3,4,5-triol of compound of formula V.

Formula V

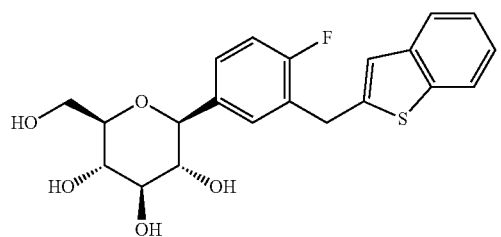

11. The process according to claim 1, wherein, the base used in step a) is selected from the group consisting of n-butyl lithium, sec-butyl lithium, n-hexyl lithium, (trimethylsilyl)methyl lithium, and mixtures thereof.

12. The process according to claim 1, wherein Ar is selected from the group consisting of a residue of formula A and a residue of formula B.

13. The process according to claim 1, wherein:
the compound of Formula IX is (2S,3R,4R,5S,6R)-2-(3-((5-(4-fluorophenyl)thiophen-2-yl)methyl)-4-methylphenyl)-6-(hydroxymethyl)tetrahydro-2H-pyran-3,4,5-triol of Formula II, Formula II

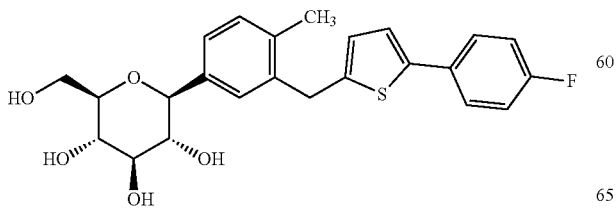

wherein, in step (a), 2,3,4,6-tetra-O-benzyl-D-glucopyranose is reacted with an aryl halide compound of Formula VII, where X is Cl, Br or I, R is methyl, and Ar is 5-(4-fluorophenyl)thiophen-2-yl, to isolate a compound of Formula Ia;

Formula Ia

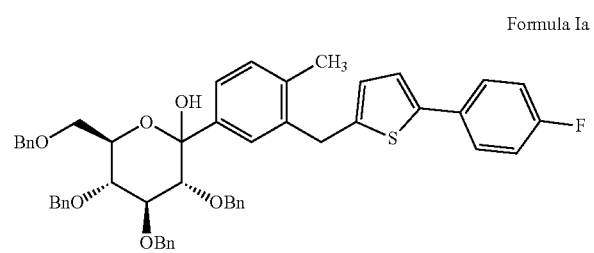

wherein, in step (b), the compound of Formula Ia is reduced to obtain a compound of Formula VIIIb; and Formula VIIIb

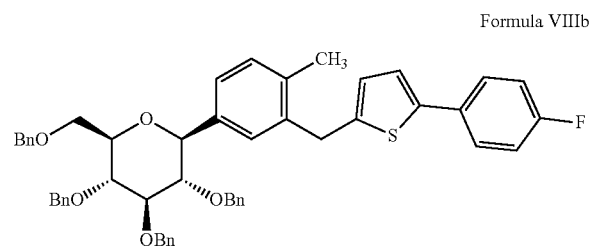

wherein, in step (c), the compound of Formula VIIIb is purified; and wherein, in step (d), the compound of Formula VIIIb is deprotected to isolate the compound of Formula II.

14. The process according to claim 13, further comprising a step of purifying the compound of formula II using a first solvent selected from the group consisting of ethyl acetate, methanol, methyl ethyl ketone, methyl isobutyl ketone, isopropyl acetate, and aqueous or nonaqueous mixtures thereof for dissolution; and using a second solvent selected from the group consisting of n-hexane, n-heptane, cyclohexane, and mixtures thereof for precipitation of the pure compound.

15. A process for the preparation of a compound of Formula IX,

Formula IX

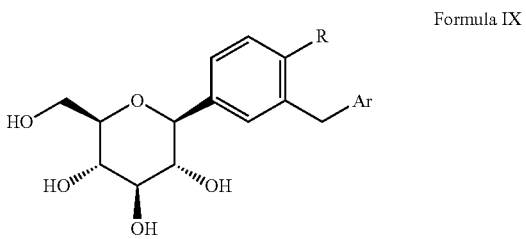

wherein R is halogen, alkyl or alkoxy group; and Ar is selected from the group consisting of a residue of formula A, a residue of formula C, and a residue of formula D:

A

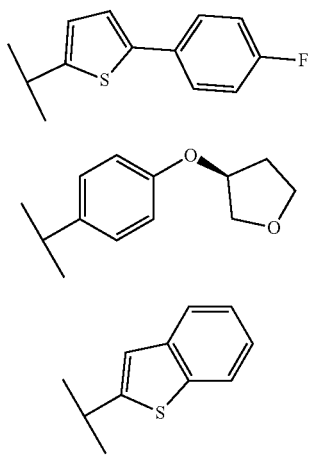

C

D said process comprising,
a) treating 2,3,4,6-tetra-O-benzyl-D-glucopyranose of Formula VI,

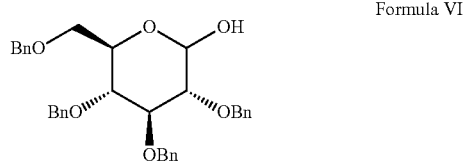 [SMILES: OC1O[C@H](COCc2ccccc2)[C@@H](OCc2ccccc2)[C@H](OCc2ccccc2)[C@H]1OCc1ccccc1]

Formula VI with an aryl halide compound of Formula VII

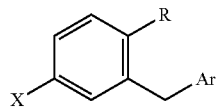

Formula VII wherein Ar and R are as previously defined and X is Cl, Br, or I in the presence of a sodium hypochlorite solution, a strong base, and an organic solvent at a temperature in the range of -80° C. to 0° C. to isolate an intermediate compound of Formula I;

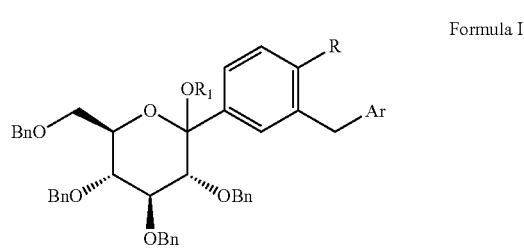

Formula I wherein Bn is Benzyl group; $R_1$ is hydrogen or methyl; and
R and Ar are as defined above,
b) reacting the intermediate compound of Formula I with triethylsilane and boron trifluoride-diethyl etherate in presence of a solvent to obtain a reaction mixture comprising an intermediate compound of Formula VIII;

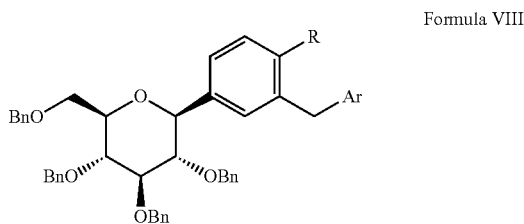

Formula VIII where R and Ar are as defined above, and
c) deprotecting the intermediate compound of Formula VIII in situ in the reaction mixture of step (b) to obtain the compound of Formula IX.

* * * * *